United States Patent [19]

Browne

[11] Patent Number: 4,785,062

[45] Date of Patent: * Nov. 15, 1988

[54] REACTION PRODUCT OF O-EPOXYALKYLATED TETRAKIS(HYDROXYPHENYL)ETHANE RESIN AND PHENOL WITH PRODUCT HAVING NO REMAINING EPOXY GROUPS

[75] Inventor: Alan R. Browne, Columbia, Md.

[73] Assignee: W. R. Grace & Co.-Conn., New York, N.Y.

[ * ] Notice: The portion of the term of this patent subsequent to Jul. 15, 2003 has been disclaimed.

[21] Appl. No.: 636,419

[22] Filed: Jul. 31, 1984

[51] Int. Cl.$^4$ ............... C08G 59/18; C08G 59/20; C08G 59/62
[52] U.S. Cl. ................... 525/523; 522/101; 522/181; 525/524; 525/534; 528/87; 528/89; 528/104; 568/640
[58] Field of Search .................. 204/159.14; 525/523, 525/524, 534; 528/87, 89, 104; 568/640; 522/101, 181

[56] References Cited

U.S. PATENT DOCUMENTS

| | | | |
|---|---|---|---|
| 3,136,637 | 6/1964 | Larson | 430/160 |
| 3,179,518 | 4/1965 | Sus et al. | 430/175 |
| 3,350,353 | 10/1967 | Alvey | 525/523 |
| 3,462,267 | 8/1969 | Giangualano et al. | 430/156 |
| 3,477,990 | 11/1969 | Dante et al. | 528/89 |
| 3,679,419 | 7/1972 | Gillich | 430/175 |
| 3,933,495 | 1/1976 | Kondo et al. | 430/303 |
| 3,948,855 | 4/1976 | Perry | 528/89 |
| 4,104,072 | 8/1978 | Golda et al. | 430/156 |
| 4,186,006 | 1/1980 | Kobayashi et al. | 430/331 |
| 4,308,185 | 12/1981 | Evans et al. | 525/534 |
| 4,483,758 | 11/1984 | Rowe et al. | 430/280 |
| 4,600,679 | 7/1986 | Browne et al. | 430/302 |

*Primary Examiner*—Charles L. Bowers, Jr.
*Attorney, Agent, or Firm*—Charles A. Cross; Richard P. Plunkett

[57] ABSTRACT

This invention is directed to the reaction product of an O-epoxyalkylated tetrakis (hydroxyphenyl) alkane resin with a phenol, which is used either as an upper layer over a lower layer of a diazo resin in a bi-layer system or as a homogeneous mixture with a diazo resin in a mono-layer system to provide a water-developable, negative-working, lithographic printing plate.

1 Claim, No Drawings

REACTION PRODUCT OF O-EPOXYALKYLATED TETRAKIS(HYDROXYPHENYL)ETHANE RESIN AND PHENOL WITH PRODUCT HAVING NO REMAINING EPOXY GROUPS

FIELD OF THE INVENTION

This invention relates to a novel, water-permeable, water-insoluble, oleophilic material operable as the upper layer per se or admixed with a diazo resin as a mono-layer to form a water-developable, negative-working, lithographic printing plate.

BACKGROUND OF THE INVENTION

This invention relates to a novel compound comprising the reaction product of an O-epoxyalkylated tetrakis (hydroxyphenyl) alkane resin with a phenol. This invention further relates to a method for the production of presensitized, lithographic printing plates and to novel lithographic printing plates obtained thereby. More particularly, this invention relates to a negative-working, water-developable, bi-layer or mono-layer lithographic printing plate comprising a substrate having a hydrophilic surface, said surface being either (a) first coated with a layer of a water-soluble, lithographically suitable, photosensitive, negative-working, aromatic diazo compound and top coated with a layer of the water-permeable, water-insoluble, oleophilic resin layer of the aforesaid reaction product or (b) a homogeneous mixture of the aromatic diazo composition and the aforesaid reaction product in a mono-layer system, such systems both providing a water-developable, negative-working, lithographic printing plate. Upon imagewise exposure, the exposed areas become water-insoluble and development is affected by washing away the unexposed areas with tap water.

The art in the lithographic printing plate area has always had a problem with development of the image. That is, various chemical developing substances are employed which must be discarded usually through community waste removal facilities. Not only are such developers costly to purchase but they also cause pollution problems on being discarded. Thus, a lithographic printing plate which is developable by ordinary tap water is commercially desirable.

DESCRIPTION OF THE PRIOR ART

Reactions of polyglycidyl ethers with phenols are known in the art. U.S. Pat. No. 3,477,990 teaches the reaction of glycidyl ethers of novolak resins with phenols. Additionally, U.S. Pat. No. 3,948,855 teaches the reaction of polyepoxides, e.g., glycidyl ethers of novolak resins with phenol. However, the use of materials containing the novolac resins is precluded in lithographic plates as described herein since these materials are not water permeable. U.S. Pat. No. 3,350,353 teaches the reaction of epoxide resins with phenols. However, the resultant product is a liquid and thus not usable to form a lithographic printing plate since the imaged transparency in contact therewith would stick to the liquid during exposure.

Bi-layer lithographic printing plates are also known in the art. A presensitized, lithographic plate having an organophilic, polymeric surface overlaying a light sensitive diazo layer supported by a hydrophilic surfaced base is described in U.S. Pat. No. 3,136,637. The overlayer exists in a polymeric state both before and after exposure of the plate and the actinic light received during exposure acts solely on the underlying light sensitive diazo resin to cause insolubilization thereof in the exposed areas. The plate is developable as a result of the differential soft mobility or solubility between the exposed and unexposed areas of the diazo resin layer. However, during development the overcoated resin layer due to its uniform nature tends to be removed in both the exposed areas as well as in the unexposed areas thereby negating its effective use. U.S. Pat. No. 3,462,267. describes an improvement on the above system whereby the organophilic layer is a photocrosslinkable polymer which is insolubilized by the crosslinking action of pendant photolabile groups in the exposed area. However, the system also has the drawback that the organophilic layer of such lithographic plates is not developable in the same solutions as used for the diazo resin, necessitating two or more developing steps.

U.S. Pat. No. 3,179,518 teaches in the manufacture of lithographic printing plates the use of certain water soluble diazo type compositions which become water-insoluble upon imagewise exposure to UV radiation. Although this method allows for removal of non-exposed areas by development with water, the remaining imaged area cannot withstand the strain of prolonged printing, thereby requiring that an ink receptive lacquer or other similar coating be applied to the imaged area after development. Thus, it is this coating which actually prints the desired image and not the diazo.

U.S. Pat. No. 4,104,072 teaches a water-developable, lithographic printing plate consisting of a diazo layer on an aluminum sheet, said diazo layer being top coated with a layer consisting of an oleophilic resin in combination with a lithographically suitable, negative-working photosensitizer selected from the group consisting of the reaction product of the para-diazo-diphenylamine-paraformaldehyde condensate with 2-hydroxy-4-methoxy benzophenone sulfonic acid and the azido pyrenes. The photosensitizer is a necessary component which binds the resin and renders the composition water impermeable after exposure to UV radiation.

SUMMARY OF THE INVENTION

The instant invention provides a novel composition which can be used as an upper oleophilic layer, with a diazo resin composition as the lower layer, in a bi-layer lithographic printing plate. The composition also can be used in direct combination with a diazo resin in a mono-layer, lithographic printing plate. The invention also provides a lithographic printing plate which may be developed by use of ordinary tap water. The present invention further provides a light sensitive plate comprising a substrate having a hydrophilic surface which surface is first coated with a layer of a water soluble, lithographically suitable, photosensitive, negative-working, aromatic diazo composition and top coated with an oleophilic layer of a water-permeable, water-insoluble, oleophilic reaction product of an O-epoxyalkylated tetrakis (hydroxyphenyl) alkane resin and a substituted or unsubstituted phenol. The invention also provides a mono-layered lithographic plate of a mixture of said diazo and oleophilic layers which is water-developable. Upon imagewise exposure to actinic radiation, the exposed areas become water-insoluble and development is conveniently and efficiently performed by washing away the unexposed areas with tap water.

The resultant presensitized sheet exhibits good storage ability.

DETAILED DESCRIPTION OF THE INVENTION

The instant invention is directed to a novel oleophilic compound and to its use in a water-developable, lithographic printing plate.

The first step in forming said plate is to provide a substrate. Suitable substrates for lithographic plates include metals (e.g., aluminum, copper, zinc), glass, paper and the like. Prior to application of the diazo resin to the surface of such substrates for lithographic purposes, it is generally necessary to passivate the surface to prevent any deleterious interaction between the surface and the diazo resin. Such passivating treatments may also help promote a firm bond between the exposed portions of the diazo resin and the substrate and they also aid in providing a hydrophilic surface during the lithographic printing process. The silicate treatment described in U.S. Pat. No. 2,714,066 is the preferred passivating treatment for metal substrates. Other passivating treatments are disclosed in U.S. Pat. Nos. 2,946,638 (zirconium hexahalide), 3,201,247 (phosphomolybdate treatment) and 3,148,984. Suitable coating techniques used to accomplish the same purpose are described in U.S. Pat. Nos. 3,161,517 and 3,196,785.

The water-soluble, lithographically suitable, photosensitive, negative-working, aromatic diazo compositions used as the first layer are known in the art and include polymeric diazonium compounds such as the reaction product of para-diazo diphenylamine with paraformaldehyde e. g., the condensation product of 4-diazodiphenylamine sulphate with formaldehyde and zinc chloride as the preferred diazonium compounds. Other diazonium compounds operable herein include, but are not limited to, 4-diazodiphenylamine sulfate,
1-diazo-4-N,N-dimethylaminobenzene zinc chloride,
1-diazo-4-N,N-diethylaminobenzene zinc chloride,
1-diazo-4-N-ethyl-N-hydroxyethylaminobenzene, ½ zinc chloride,
1-diazo-4-N-methyl-N-hydroxyethylaminobenzene, ½ zinc chloride,
1-diazo-2,5-diethoxy-4-benzoylaminobenzene, ½ zinc chloride,
1-diazo-4-N-benzylaminobenzene, ½ zinc chloride,
1-diazo-4-N,N-dimethylaminobenzene borofluoride,
1-diazo-4-morpholinobenzene, ½ zinc chloride,
1-diazo-4-morpholinobenzene borofluoride,
1-diazo-2,5-dimethoxy-4-p-tolylmercaptobenzene, ½ zinc chloride,
1-diazo-2-ethoxy-4-N,N-dimethylaminobenzene, ½ zinc chloride,
p-diazo-dimethyl aniline, ½ zinc chloride,
1-diazo-4-N,N-diethylaminobenzene, ½ zinc chloride,
1-diazo-2,5-dibutoxy-4-morpholinobenzene sulfate,
1-diazo-2,5-diethoxy-4-morpholinobenzene, ½ zinc chloride,
1-diazo-2,5-dimethoxy-4-morpholinobenzene, zinc chloride,
1-diazo-2,5-diethoxy-4-morpholinobenzene, ½ zinc chloride,
1-diazo-2,5-diethoxy-4-morpholinobenzene borofluoride,
2-diazo-1-naphthol-5-sulfonic acid, sodium salt,
1-diazo-4-N,N-diethylaminobenzene, borofluoride,
1-diazo-2,5-diethoxy-4-p-tolylmercaptobenzene, ½ zinc chloride,
1-diazo-3-ethoxy-4-N-methyl-N-benzylaminobenzene, ½ zinc chloride,
1-diazo-3-chloro-4-N,N-diethylaminobenzene, ½ zinc chloride,
1-diazo-3-methyl-4-pyrrolidinobenzene chloride, zinc chloride, 1-diazo-3-methyl-4-pyrrolidinobenzene borofluoride,
1-diazo-2-chloro-4-N,N-dimethylamino-5-methoxybenzene, borofluoride and
1-diazo-3-methoxy-4-pyrrolidinobenzene, zinc chloride. Such materials are commercially available.

The top coat layer is a water-permeable, waterinsoluble, oleophilic reaction product of an O-epoxyalkylated tetrakis (hydroxyphenyl) ethane resin and a substituted or unsubstituted phenol. The oleophilic resin is formed by reacting the O-epoxyalkylated tetrakis (hydroxyphenyl) ethane resin with a substituted or unsubstituted phenol as will be shown by examples hereinafter and has the formula:

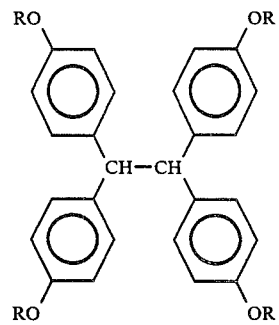

wherein R is

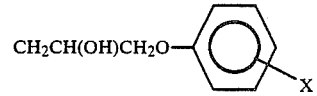

and X is H, halogen, alkoxy containing 1 to 8 carbon atoms, alkyl containing 1 to 14 carbon atoms, aryl containing 6 to 14 carbon atoms and aralkyl containing 6 to 14 carbon atoms. One O-epoxyalkylated tetrakis (hydroxyphenyl) ethane resin which is commercially available is EPON-1031 from Shell Oil Co.

Epoxy compounds are known to react with phenolic OH groups to form aromatic hydroxy ethers. Catalysts used to effect the reaction are inorganic and organic bases, phosphonium halides, tertiary amines and quaternary ammonium salts.

In the instant invention, the O-epoxyalkylated tetrakis (hydroxyphenyl) ethane resin is reacted with one equivalent of a substituted or unsubstituted phenol per epoxy group in the presence of between one tenth and one fiftieth of an equivalent of a quaternary ammonium salt, the preferred catalyst being hexadecyltrimethyl ammmonium bromide. Solutions of the reactants are heated together in a suitable solvent with stirring at temperatures between 60° C. and 85° C. for periods of between 12 and 60 hours until no epoxide groups remain as shown by NMR analysis. Suitable solvents include, but are not limited to, methyl ethyl ketone, methyl isobutyl ketone and ethyl acetate.

The aromatic diazo composition is applied as an aqueous solution (2–10% by weight) by any suitable means such as roll coating, whirl coating, spraying or hand wiping onto the suitable base sheet. After drying, the oleophilic resin is applied as an organic solution (2–10% by weight) by any suitable means as described for the diazo composition. Solvents used with said oleophilic resin include, but are not limited to, methyl ethyl ketone, methyl isobutyl ketone, acetone and methyl cellosolve. The diazo composition and the oleophilic resin can also be combined in a mono-layer by applying a coating as a solution of a mixture of diazo composition and oleophilic resin, by any suitable means as described above for the diazo composition.

Suitable solvent systems used to apply the combined mono-layer include, but are not limited to, dimethyl sulfoxide, dimethyl formamide, ethylene dichloride, methoxyethanol and mixtures of the above.

In the case of the bi-layer plate, the diazo layer is applied to the base sheet at a coating weight of from about 5 to about 200 mg/sq. ft., preferably from about 10 to about 100 mg/sq. ft. The coating weight of the oleophilic top coat layer is from about 5 to about 300 mg/sq. ft. with a preferred range of from about 35 to about 200 mg/sq. ft.

In the case of the mono-layer plate, the combined layer containing 20 to 80% of diazo composition, preferably between 40 and 70%, balance oleophilic resin is applied to the base sheet at a coating weight of from about 5 to about 200 mg/sq.ft. for both the diazo composition and the oleophilic resin, with a preferred range of from about 10 to about 100 mg/sq.ft.

As used herein, the term "water-permeable" means that the composition is insoluble in water but that water is able to permeate through a thin layer of the composition. In the instant invention in the case of the bi-layer plate, the upper water-insoluble, oleophilic resin layer is water-permeable and remains water-permeable in the unexposed area after imagewise exposure. However, the lower diazo composition layer is initially water-soluble and becomes water-insoluble in the exposed area while remaining water-soluble in the unexposed area. Furthermore, in the exposed area the diazo composition binds together both with itself and also the base substrate and the upper oleophilic resin layer. Thus, on developing an exposed plate with water, the water permeates the upper oleophilic layer in the unexposed region and dissolves the water-soluble, unexposed diazo composition thereunder allowing both layers to be removed from the plate thus exposing the base substrate. In the exposed image area the diazo composition is no longer water soluble and thus neither the upper oleophilic layer nor the diazo composition layer is removed. Since the image areas are oleophilic and ink receptive, while the non-image area, i. e., base substrate, is by its nature hydrophilic and oleophobic, a lithographic plate results.

In the instant invention in the case of the mono-layer plate, the water-insoluble, water-permeable, oleophilic resin is intimately mixed with the water soluble diazo composition. The diazo composition becomes waterinsoluble in the exposed area while remaining watersoluble in the unexposed area. Furthermore, in the exposed area the diazo composition binds together both with itself and also the base substrate and the surrounding oleophilic resin.

Thus, on developing an exposed plate with water, the water permeates the oleophilic resin and dissolves the water-soluble, unexposed diazo resin allowing both to be removed from the plate thus exposing the base substrate. In the exposed image area the diazo composition is no longer water-soluble and thus neither the oleophilic resin nor the diazo composition is removed. Since the image areas are oleophilic and ink receptive, while the non-image area, i. e., base substrate, is by its nature hydrophilic and oleophobic, a lithographic plate results.

The following examples are set out to explain, but expressly not limit, the instant invention. Unless otherwise noted, all parts and percentages are by weight.

EXAMPLE 1

To a 500 ml round bottom flask equipped with a condenser and magnetic stirrer were charged 20.0 g of an epoxy resin sold under the tradename "EPON-1031" by Shell Oil Co., 12.0 g of phenol, 3.0 g of hexadecyltrimethyl ammonium bromide as catalyst and 250 ml of methyl ethyl ketone. The flask was heated and the resulting stirred solution allowed to reflux for 24 hours. The reaction product was allowed to cool and then concentrated. The reaction product structure, i.e.,

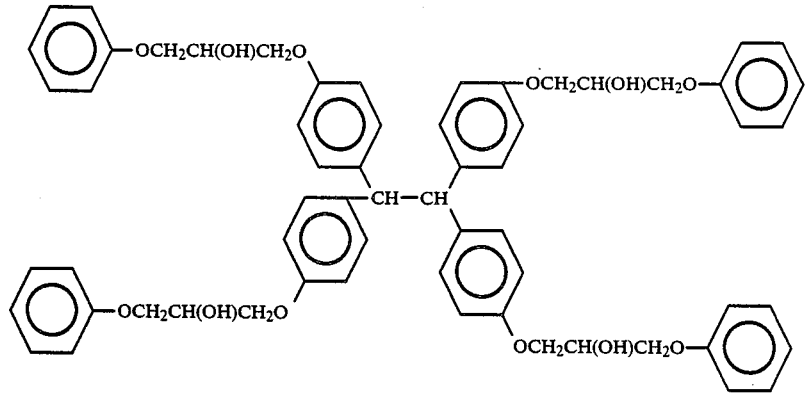

was confirmed by NMR.

EXAMPLE 2

To a 250 ml round bottom flask equipped with a condenser and magnetic stirrer were charged 10.0 g of an epoxy resin sold under the tradename "EPON-1031" by Shell Oil Co., 11.13 g of 4-bromophenol, 2.0 g of hexadecyltrimethyl ammonium bromide as catalyst and 125 ml of methyl ethyl ketone. The flask was heated and the resulting stirred solution allowed to reflux for 24 hours. The reaction product was allowed to cool and then concentrated. The reaction product structure, i.e.,

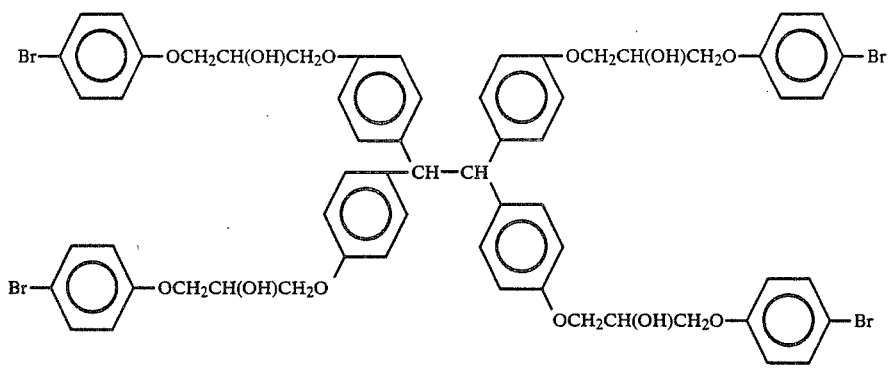

was confirmed by NMR.

EXAMPLE 3

To a 250 ml round bottom flask equipped with a condenser and magnetic stirrer were charged 10.0 g of an epoxy resin sold under the trandname "EPON-1031" by Shell Oil Co., 9.7 g of 4-t-butyl phenol, 2.0 g of hexadecyltrimethyl ammonium bromide as catalyst and 125 ml of methyl ethyl ketone. The flask was heated and the resulting stirred solution allowed to reflux for 24 hours. The reaction product was allowed to cool and then concentrated. The reaction product structure, i.e.,

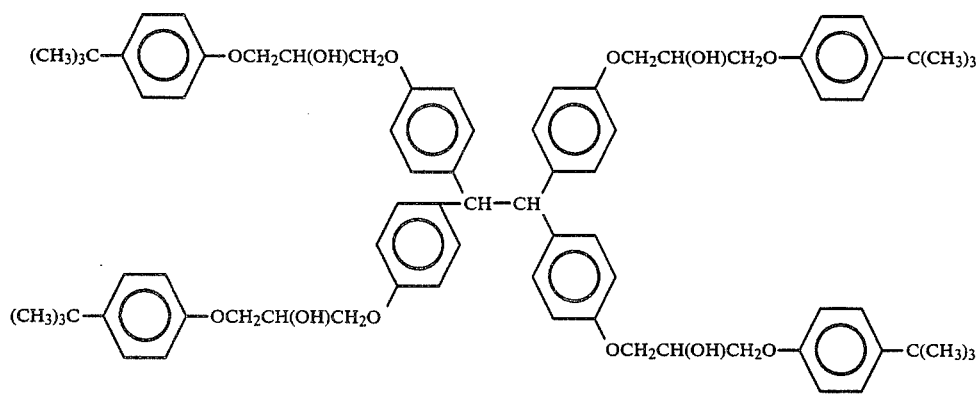

was confirmed by NMR.

EXAMPLE 4

A solution of a diazo composition was prepared by dissolving 20 g of a diazo resin sold under the tradename "Diazo Resin No. 4, Type L" by Fairmount Chemical Co., Inc. in 500 ml of water. The coating was applied to three LKK silicated aluminum lithographic plates manufactured by Anchor/Lith-Kem-Ko using a Western Lithocoater roll coater. Each of the dried plates was then recoated in the same manner with a solution of the product from Example 1 prepared by dissolving 10 g of the product in 250 ml of methyl isobutyl ketone.

EXAMPLE 5

Two additional plates were prepared by the method of Example 4 except that the product from Example 1 was replaced with the products from Examples 2 and 3.

EXAMPLE 6

The presensitized plates obtained in Examples 4 and 5 were exposed through a contacting negative to a 1,000 W mercury lamp at a distance of 22 inches in a NuArc N1000 Platemaker set at 25 units exposure. The exposed plates were developed with tap water in 5 seconds and treated with Western A.G.E. finisher. The resulting plates readily accepted ink and printed clean good quality copies.

EXAMPLE 7

A solution was prepared by dissolving 20 g of a diazo resin sold under the tradename "Diazo Resin No. 4, Type L" by Fairmount Chemical Co., Inc. and 20 g of the reaction product of Example 1 in 500 ml of dimethylsulfoxide. The coating was applied to an LKK silicated aluminum lithographic plate manufactured by Anchor/Lith-Kem-Ko using a Western Lithocoater roll coater. The dried plate was exposed through a contacting negative to a 1000 W mercury lamp at a distance of 22 inches in a NuArc N1000 Platemaker set at 25 units exposure. The exposed plate was developed with tap water in 10 seconds and treated with Western A.G.E. finisher. The resulting plate readily accepted ink and printed clean good quality copies.

I claim:

1. A composition comsisting of the reaction product of an O-epoxyalkylated tetrakis (hydroxyphenyl) ethane resin and sufficient substituted or unsubstituted phenol to react with all the epoxy groups, said reaction product being a group member of the formula:

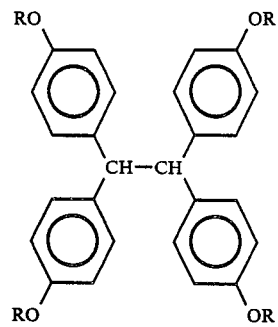

wherein R is

—CH$_2$CH(OH)CH$_2$O—⟨phenyl⟩—X and X is H, halogen, alkoxy containing 1 to 8 carbon atoms, alkyl containing 1 to 14 carbon atoms, aryl containing 6 to 14 carbon atoms and aralkyl containing 6 to 14 carbon atoms.

* * * * *